US009375692B2

(12) United States Patent
Greter et al.

(10) Patent No.: US 9,375,692 B2
(45) Date of Patent: Jun. 28, 2016

(54) MIXING DEVICE FOR A DISCHARGE UNIT

(71) Applicant: MEDMIX SYSTEMS AG, Rotkreuz (CH)

(72) Inventors: Andy Greter, Rotkreuz (CH); Manuel Furrer, Beinwil/Freiamt (CH); Martin Veid, Weggis (CH)

(73) Assignee: MEDMIX SYSTEMS AG, Rotkreuz (CH)

( * ) Notice: Subject to any disclaimer, the term of this patent is extended or adjusted under 35 U.S.C. 154(b) by 0 days.

(21) Appl. No.: 14/419,995

(22) PCT Filed: Jul. 9, 2013

(86) PCT No.: PCT/CH2013/000121
§ 371 (c)(1),
(2) Date: Feb. 6, 2015

(87) PCT Pub. No.: WO2014/029035
PCT Pub. Date: Feb. 27, 2014

(65) Prior Publication Data
US 2015/0190770 A1    Jul. 9, 2015

(30) Foreign Application Priority Data

Aug. 21, 2012  (CH) ..................... 1432/12

(51) Int. Cl.
*B67D 7/78*     (2010.01)
*B01F 15/02*    (2006.01)
(Continued)

(52) U.S. Cl.
CPC ........... *B01F 15/0237* (2013.01); *B01F 5/0645* (2013.01); *B01F 5/0661* (2013.01);
(Continued)

(58) Field of Classification Search
CPC ................ B05C 17/00566; B05C 17/00593; B05C 17/00553; B05C 17/00503; B01F 15/0237; B01F 5/0645; B01F 5/0646; B01F 5/0661; B01F 13/0023; B01F 2005/0022; A61M 5/19; A61B 2017/00495
USPC .............. 222/145.6, 145.5, 94, 129; 366/349, 366/336–341
See application file for complete search history.

(56) References Cited

U.S. PATENT DOCUMENTS 3,328,003 A   6/1967  Chisholm
3,927,868 A  12/1975  Moore
(Continued)

FOREIGN PATENT DOCUMENTS

EP    0 815 929 A1   1/1998
EP    2 018 132      1/2009
(Continued)

OTHER PUBLICATIONS

International Search Report of PCT/CH2013/000121 dated Oct. 25, 2013.
(Continued)

*Primary Examiner* — Lien Ngo
(74) *Attorney, Agent, or Firm* — Sughrue Mion, PLLC

(57) ABSTRACT

A mixing device which can be connected to a discharge unit and is provided to mix one or more substances together as they are discharged from the discharge unit. The mixing device has a base element with a circumferential side wall and an insert which can be inserted into the base element in such a manner that at least one circumferential zone of said insert lies against the side wall of the base element in a sealing manner. A mixing structure with mixing channels is formed on the insert, through which mixing structure the substances can be discharged from the discharge unit.

13 Claims, 7 Drawing Sheets

(51) Int. Cl.
  *B05C 17/005* (2006.01)
  *B01F 5/06* (2006.01)
  *B01F 13/00* (2006.01)
  *B01F 5/00* (2006.01)
  *A61M 5/19* (2006.01)
  *A61B 17/00* (2006.01)

(52) U.S. Cl.
  CPC ....... *B01F13/0023* (2013.01); *B05C 17/00553* (2013.01); *B05C 17/00593* (2013.01); *A61B 2017/00495* (2013.01); *A61M 5/19* (2013.01); *B01F 2005/0022* (2013.01); *B05C 17/00503* (2013.01)

(56) References Cited

U.S. PATENT DOCUMENTS

| | | | |
|---|---|---|---|
| 3,989,434 A * | 11/1976 | Mercer | B29C 45/581 366/96 |
| 4,027,857 A | 6/1977 | Cunningham | |
| 4,261,481 A | 4/1981 | Speer | |
| 4,978,336 A | 12/1990 | Capozzi et al. | |
| 5,605,255 A | 2/1997 | Reidel et al. | |
| 5,944,419 A | 8/1999 | Streiff | |
| 7,325,970 B2 * | 2/2008 | Keller | B01F 5/0617 366/337 |
| 7,841,765 B2 * | 11/2010 | Keller | B01F 5/0617 366/338 |
| 8,376,187 B2 * | 2/2013 | Keller | B65D 81/325 222/137 |
| 2003/0048694 A1 | 3/2003 | Horner et al. | |
| 2008/0029542 A1 | 2/2008 | Keller | |
| 2008/0056065 A1 | 3/2008 | Keller | |
| 2008/0089173 A1 | 4/2008 | Lu et al. | |
| 2010/0163579 A1 * | 7/2010 | Keller | B05C 17/00506 222/137 |
| 2011/0139821 A1 | 6/2011 | Greter et al. | |
| 2011/0228631 A1 | 9/2011 | Stoeckli et al. | |
| 2012/0175384 A1 | 7/2012 | Greter et al. | |
| 2013/0023833 A1 | 1/2013 | Kayser | |

FOREIGN PATENT DOCUMENTS

| | | |
|---|---|---|
| WO | 88/03052 A1 | 5/1988 |
| WO | 2006/005205 A1 | 1/2006 |
| WO | 2006/039827 A1 | 4/2006 |
| WO | 2007/131371 A1 | 11/2007 |
| WO | 2010/009563 A1 | 1/2010 |
| WO | 2010/031197 A1 | 3/2010 |
| WO | 2011/035449 A2 | 3/2011 |
| WO | 2011/078790 A1 | 6/2011 |
| WO | 2011/116484 A1 | 9/2011 |

OTHER PUBLICATIONS

International Preliminary Report on Patentability dated Mar. 5, 2015 issued by the International Searching Authority in counterpart Application No. PCT/CH2013/000121.

* cited by examiner

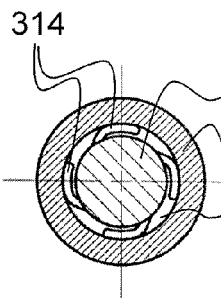 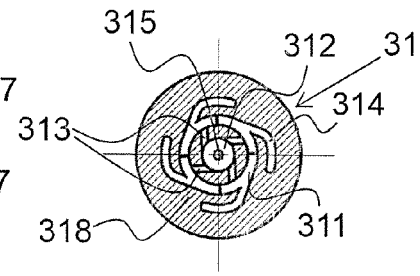 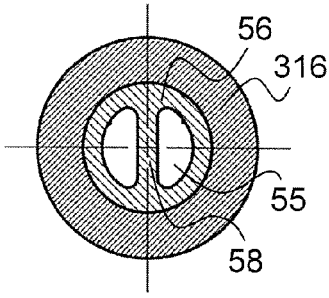
FIG. 8  FIG. 9  FIG. 10
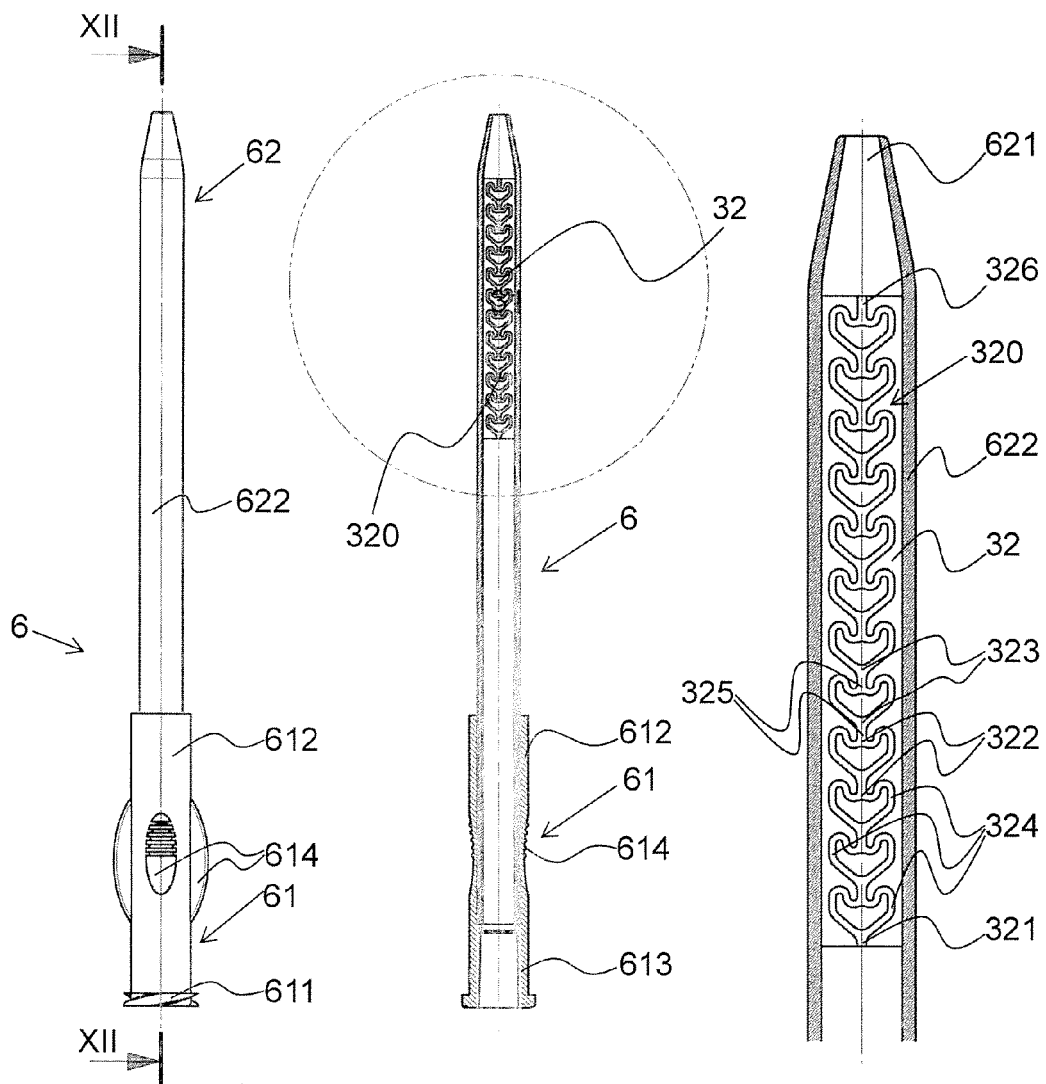
FIG. 11  FIG. 12  FIG. 13

MIXING DEVICE FOR A DISCHARGE UNIT

CROSS REFERENCE TO RELATED APPLICATIONS

This is a National Stage of International Application No. PCT/CH2013/000121 filed Jul. 9, 2013, claiming priority based on Swiss Patent Application No. 01432/12 filed Aug. 21, 2012, the contents of all of which are incorporated herein by reference in their entirety.

TECHNICAL SCOPE

The present invention relates to a mixing device which is connectable to a discharge unit and which, when one or more substances are discharged from the discharge unit, serves for mixing said substances. The mixing device is in particular a static mixer. The invention also relates to a set comprising a discharge unit and a mixing device of this type.

PRIOR ART

Mixing devices and in particular so-called static mixers are often used in medical applications but also in other applications in order to mix two or even more substances together when they are discharged from a discharge unit. The substances to be mixed together, in this case, are usually stored in a discharge unit with separate reservoirs, such as, for example, a double or multiple syringe. When the substances are discharged from the discharge unit by means of a piston in a distal direction, the substances are then mixed inside the mixing device, which is connected to the discharge unit, to form as homogenous a mixture as possible. Flow-influencing elements, which bring about turbulence in the fluid flow in order to obtain a mixing of the substances as a result, are usually provided in the interior of the mixing device.

These types of mixing devices, however, can also serve for the purpose of homogenizing a single substance stored in a discharge unit with reference to composition, temperature or density differences.

Examples of these types of mixing devices are disclosed in documents US 2003/0048694, U.S. Pat. No. 5,944,419, EP 0 815,929, U.S. Pat. No. 3,328,003 and US 2011/0228631.

The majority of these known static mixers, however, are unsuitable for low-viscosity liquids as well as in the case of small volumes and low flow rate because too few turbulent flows are generated and consequently the mixing of the substances can be unsatisfactory. In addition, in the case of the conventional mixers the dead volumes are relatively large. In the case of substances which react quickly with one another, there is the additional problem of a chemical reaction being able to take place even in the interior of the mixing device, as a result of which the substances can become "blocked" in the mixing device. Consequently, the shortest possible dwell time for the substances in the mixing device is the aim.

U.S. Pat. No. 4,978,336 discloses a mixing device where the substances pass by means of separate channels into a mixing chamber in which they are mixed together, directly before they pass to the outside by means of a spray nozzle. Document U.S. Pat. No. 5,605,255 describes a mixing device where a cylindrical insert part is inserted in such a manner into a housing that the substances to be mixed are guided through a narrow space between the insert part and the housing to a mixing space which is arranged at the distal end of the insert part. Sufficient mixing, however, is not ensured in the case of the mixing devices disclosed in said documents either, in particular in the case of small volumes and where the flow rate of the substances to be mixed is low.

In the case of the device described in EP 2 018 132, the substances are pre-mixed before reaching the actual mixing chamber. The dead volume generated in said device, however, is relatively large.

SUMMARY OF THE INVENTION

It is, therefore, an object of the present, invention to provide a mixing device which can be connected to a discharge unit and which ensures sufficient mixing in particular of small quantities of low-viscosity substances with as small a dead volume as possible. The mixing device should additionally comprise a compact design and should be able to be produced in as simple and cost-efficient a manner as possible.

The present invention therefore provides a mixing device which is connectable to a discharge unit and which, when one or more substances are discharged from the discharge unit, serves for mixing said substances. The mixing device comprises a base element with a circumferential side wall as well as an insert part which is insertable into the base element in such a manner that it abuts sealingly against the side wall of the base element by way of at least one circumferential region. A mixing structure with mixing channels, through which the substances can be discharged out of the discharge unit, is realized on the insert part.

This type of development of the mixing device allows it to mix in particular low-viscosity substances in an optimum manner with one another inside the mixing structure at a minimum dead volume even in the case of small volumes. As a result of the mixing device comprising a base element and an insert part which can be inserted therein, the mixing device can be produced in a very cost-efficient and in particular compact manner.

The distal direction relates below in each case to that direction in which the substances are discharged in the correct manner from the discharge unit along a main flow direction and through the mixing device. The proximal direction extends in the direction opposite this.

Advantageously, the insert part comprises as a whole a substantially cylindrical form. The base element preferably comprises a substantially hollow-cylindrical form with an at least slightly tapering inside radius which progresses advantageously in the distal direction.

The mixing channels of the mixing structure normally have a clearly defined design, which means that the fluid flow is directed in the mixing channels in each case in clearly defined paths. With the insert part inserted completely into the base element, the mixing channels preferably form in each case hose-like or tubular structures, meaning that the individual mixing channels comprise in each case a certain longitudinal portion which is non-branched and not intersected by other mixing channels.

Preferably, the circumferential region, by way of which the insert part abuts sealingly against the .side wall of the base element, represents a large part of the entire circumferential region of the insert part. Preferably, the insert part consequently abuts sealingly against the side wall of the base element by way of at least 50%, more preferably by way of at least 70% and most preferably by way of at least 90% of its circumferential surface.

The discharge unit can be, in particular, a double or multiple syringe where different substances which are to be mixed together when discharged, are stored in different reservoirs. The substances can also be stored in the reservoirs of different individual syringes which can be connected together in particular in the region of the proximal pressure faces of their pistons. In addition, the distal outlet openings of the individual syringes can also be connected together, for example by means of a connection part which brings the outlet openings together to form one common connection for the mixing device. However, the discharge unit can also be one single individual syringe where the substances, for example, are already stored in a common reservoir, but are not yet sufficiently mixed together. As an alternative to this, it can also be a discharge unit with one single substance which is to be homogenized when discharged with reference to density or temperature.

The mixing device can be accommodated in different connection elements and, in particular, can be realized as a spray head, a cannula or a catheter.

In a preferred embodiment, the mixing structure is realized at the side in the circumferential region of the insert part. The mixing structure is then consequently realized with its mixing channels in the. outside surface of the insert part, the mixing channels being realized in particular open to the outside. The insert part then delimits the mixing channels together with the circumferential side wall of the base element. The mixing device can be produced in particular in a very simple and cost-efficient manner in the case of such an embodiment by the mixing structure being milled, for example, simply on the outside surface of the insert or being provided in a corresponding manner in an injection mold. The mixing structure usually extends over the entire length of the insert part in the distal direction.

Preferably, the mixing structure is realized in the form of indentations in the outside wall of the insert part and is designed in this case in particular in a groove-shaped manner. The mixing channels are then formed, therefore, by indentations or grooves which are realized on the outside surface of the insert part. Preferably, the mixing structure comprises a maximum depth which is not greater than half, more preferred than a third, of the radius of the insert part if the insert part is designed in a substantially cylindrical manner. The dead volume of the mixing device can be kept very small in particular in this way.

Advantageously, the mixing structure comprises at least one pair of two channels, which extend separately from one another, as well as a mixing zone into which the two channels, which extend separately from one another, open out. By means of said two channels, which extend separately from one another, the fluid flow is consequently guided in particular in such a manner into a mixing zone that a turbulent flow which results in a mixing of the substances is generated in said mixing zone.

Projected along the main flow direction, along which the substances are discharged from the discharge unit and through the mixing device, the two channels, which extend separately from one another, advantageously extend both in the main flow direction and in the direction pointing opposite to the main flow direction. Preferably, the mixing channels consequently comprise portions which are traversed by the fluid flow substantially in the main flow direction, that is in the distal direction, and also portions which are traversed by the fluid flow substantially in the direction pointing opposite to the main flow direction, that is in the proximal direction.

In order to achieve a turbulent flow in the mixing zone, the two channels, which extend separately from one another, open out advantageously in such a manner into the mixing zone that the substances pass into the mixing zone from directions which are substantially opposite to one another. The fluid flows, in this case, can be slightly biased in each case in the main flow direction when entering into the mixing zone.

Thus, the channels, which extend separately from one another, advantageously open out into the mixing zone from substantially opposite directions.

More advantageously, the two channels, which extend separately from one another, even open out into the mixing zone in such a manner that the substances, projected along the main flow direction, in each case pass into the mixing zone in the direction pointing opposite to the main flow direction. The channels, which extend separately from one another, are therefore biased in each case at least slightly into the direction pointing opposite to the main flow direction in the regions where they open out into the mixing zone. As the fluid flow then leaves the mixing zone usually in the distal direction, a very turbulent flow can be brought about in this manner.

Preferably, the mixing structure comprises at least one transfer channel and one separating region into which the transfer channel opens out and from which the two channels, which extend separately from one another, extend. The mixing of the substances in the mixing structure then therefore is based on the fundamental principle that the fluid flow guided in the transfer channel is divided in the parting region into two separate fluid flows which are then brought together again in a mixing zone under turbulent flow. The mixing structure can be realized in particular in such a manner that the mixing according to said principle is repeated multiple times. The mixing structure, in this case, comprises several pairs of channels, which extend separately from one another, and several mixing zones into which, in each case, a pair of two channels, which extend separately from one another, open out, wherein the transfer channel connects a mixing zone and a separating region together.

Normally, the two channels, which extend separately from one another and together form a pair, are arranged in the main flow direction at approximately the same level. Preferably, a large part of the mixing structure is even realized in a mirror-symmetrical manner. Preferably, one pair of two channels, which extend separately from one another, additionally forms, in each case, the approximate shape of a heart.

Preferably, the mixing structure comprises at least three, in particular at least five and most preferably even more than eight pairs of channels, which extend separately from one another, and preferably at least three, in particular at least five and most preferably even more than eight mixing zones into which, in each case, one pair of the two channels, which extend separately from one another, open out. The mixing of the substances can be further improved as a result;

Preferably, a mixing chamber and a vortex chamber are realized in the base element, which can be, for example, the housing of a spray head, the hollow needle of a cannula or a catheter hose.

Several substantially identical mixing structures, which can be arranged, in particular, on diametrically opposite sides of the insert part, are advantageously realized on the insert part.

The mixing device can comprise a Luer connector which serves for connecting the mixing device to the discharge unit. Luer connectors are adequately known to the skilled person and usually comprise cones with a standard 6% taper.

A set is also provided, comprising a discharge unit and a mixing device as specified above. The mixing device, in this case, is connectable to the discharge unit in such a manner that one or several substances can be discharged out of the discharge unit through the mixing device and at the same time can be mixed in the mixing device.

SHORT DESCRIPTION OF THE FIGURES

Preferred embodiments of the invention are described below by way of the drawings which serve purely for explanation and are not to be seen as limiting. The drawings are as follows:

FIG. 8 shows a sectional view in the plane VIII-VIII of the mixing device of FIG. 1 marked in FIG. 6;

FIG. 9 shows a sectional view in the plane IX-IX of the mixing device of FIG. 1 marked in FIG. 6;

FIG. 10 shows a sectional view in the plane X-X of the mixing device of FIG. 1 marked in FIG. 3;

FIG. 11 shows a side view of a mixing device according to a second embodiment according to the invention, in the form of a cannula;

FIG. 12 shows a central sectional view through the mixing device of FIG. 11;

FIG. 13 shows an enlarged part view of the region marked in FIG. 12;

DESCRIPTION OF PREFERRED EMBODIMENTS

Figure 1:
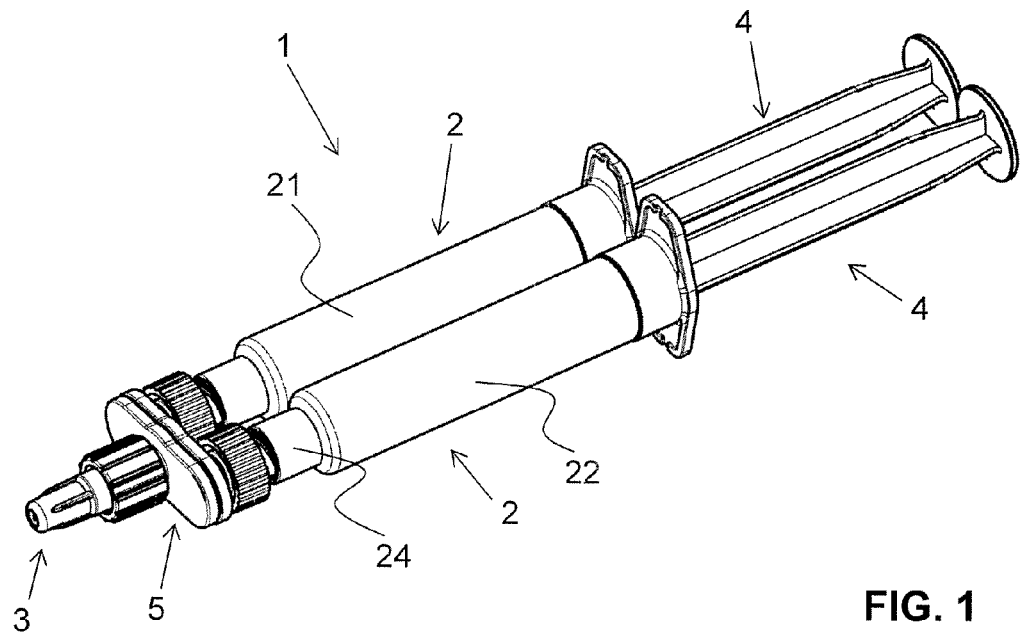
FIG. 1 shows a perspective view of a mixing device according to a first embodiment according to the invention which is connected to a discharge unit.

FIGS. 1 to 10 show a mixing device according to a first embodiment according to the invention. The mixing device is realized in this embodiment as a spray head 3 and is connected via a connection part 5 to two individual syringes 2 which are connected together. The individual syringes 2, together with the connection part 5, form a discharge unit 1.

By means of the connection part 5, the two distal outputs of the individual syringes 2 are brought together to form one single Luer connector 56 to which the spray head 3 can be connected. The spray head 3 serves in particular for mixing and atomizing the substances contained in the discharge unit 1.

The discharge unit 1 comprises, as is shown in FIGS. 1 to 5, two reservoirs 21 and 22 which are arranged in parallel and which serve for storing each of the different substances which are to be mixed together directly prior to the application or the discharging. In order to discharge the two substances preferably at the same time in each case out of an output opening which is arranged on the distal side of the reservoir 21, 22, the individual syringes 2 comprise in each case a piston 4 which is arranged so as to be displaceable in the reservoir 21 or 22. The two pistons 4 can be connected together in particular in the region of their proximal pressing faces. A device as is disclosed in WO 2010/009563 can be used, in particular, for this purpose.

In the region of their distal output openings, the reservoirs 21, 22 comprise in each case a male Luer cone 23 through which the substance which is stored in the reservoir 21 or 22 is able to be discharged in the distal direction by means of the piston 4. The male Luer cone 23, in this case, surrounds each output opening of the corresponding reservoir. In order to secure a possible connection element on the male Luer cone 23, also provided in each case are securing sleeves 24 with internal threads which are attached around each male Luer cone 23 at the distal ends of the reservoir 21, 22.

Figure 6:
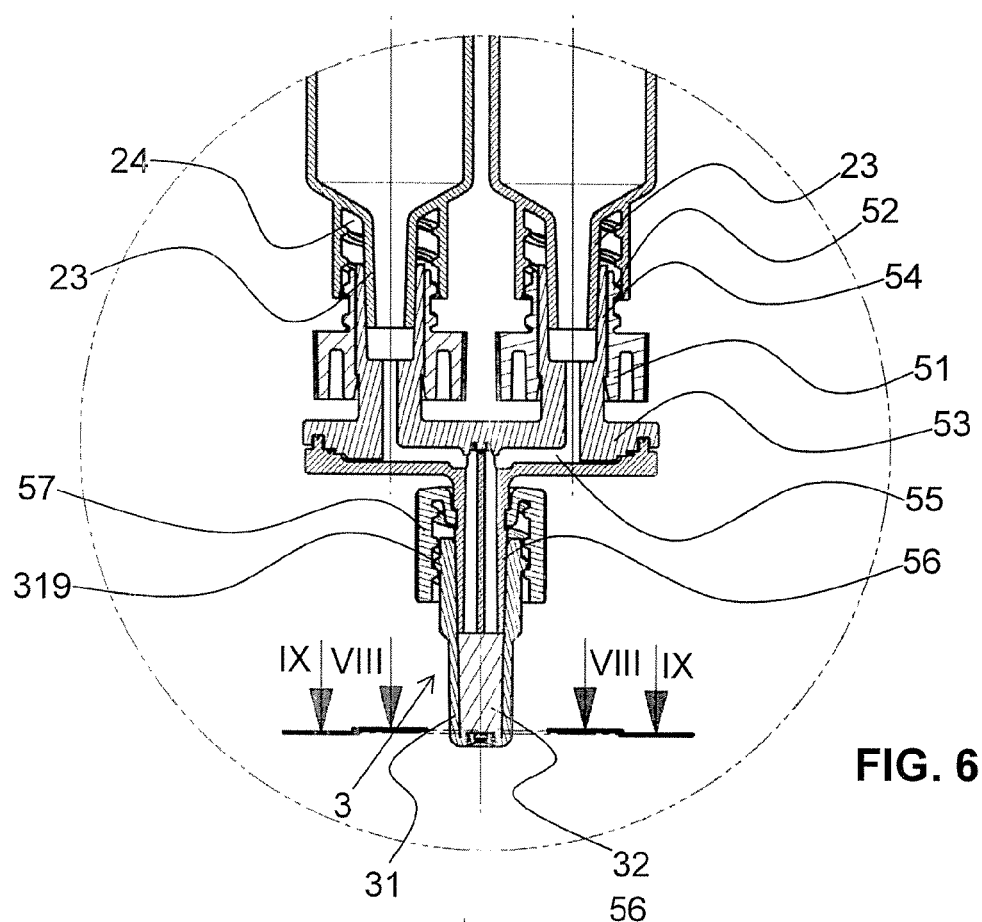
FIG. 6 shows an enlarged part view of the region marked in FIG. 3.

The design of the connection part 5, which can be seen well in particular in FIG. 6, is described in detail in WO 2011/116484. The connection part 5 essentially comprises a housing 53 with two female Luer cones 54 which point in parallel directions and serve for connecting the connection part 5 to the two male Luer cones 23 of the syringes 2. To secure the connection part 5 to the syringes 2, a rotary element 51, which can be screwed into the securing sleeve 24 of the syringes 2 by means of a threaded sleeve 52, is arranged around the female Luer cones 54. As a result, the connection part 5 can be connected sealingly to the male Luer cones 23 of the syringes 2 by way of the two female Luer cones 54. Two fluid lines 55, which extend separately from one another and in each case connect one of the female Luer connectors 54 to one of the male Luer connectors 56, are provided inside the housing 53. A separating wall 58 separates the two fluid lines 55 in the interior of the male Luer cone 56. The connection part 5 consequently comprises two separate outlet openings which open out to the outside on the distal side of the male Luer cone 56. A securing sleeve 57, which serves for securing a connection element which is connected to the male Luer cone 56, is rotationally mounted on the outside surface of the male Luer cone 56.

Figure 2:
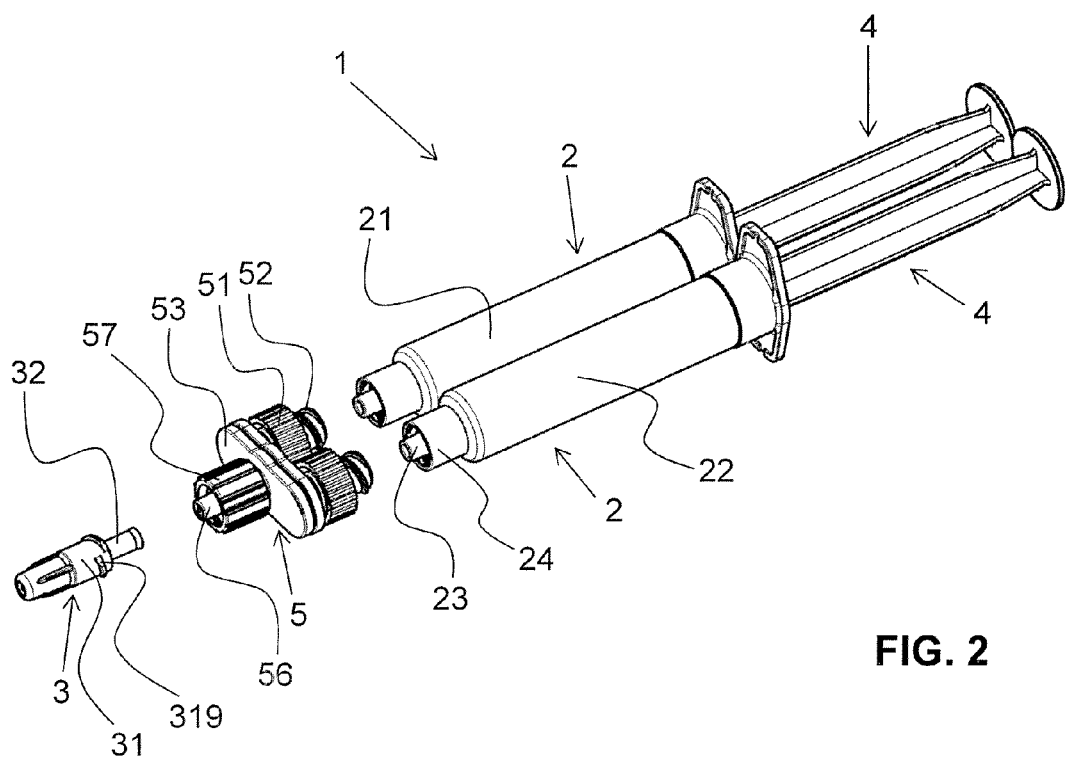
FIG. 2 shows a perspective view of the mixing device of FIG. 1, prior to connection to the discharge unit.
Figure 3:
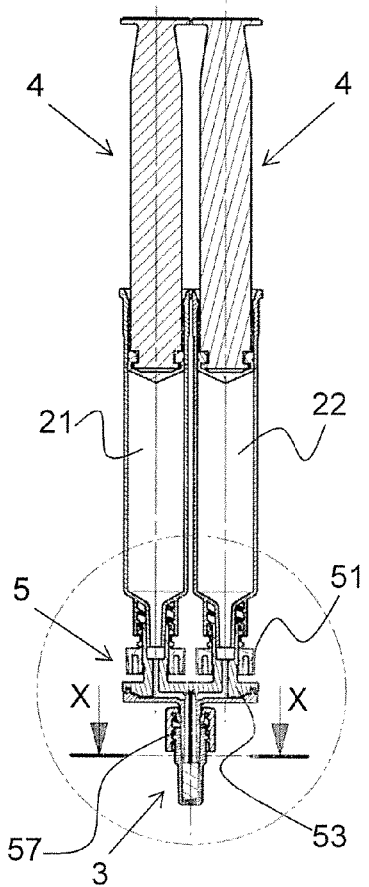
FIG. 3 shows a central sectional view in the plane III-III marked in FIG. 4 of the mixing device of FIG. 1 which is connected to a discharge unit.
Figure 4:
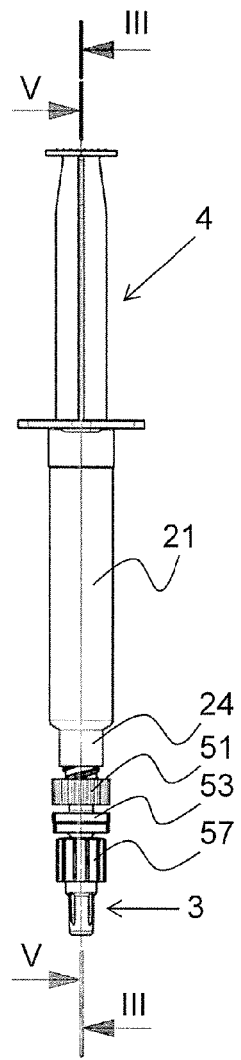
FIG. 4 shows a side view of the mixing device of FIG. 1 which is connected to a discharge unit.
Figure 5:
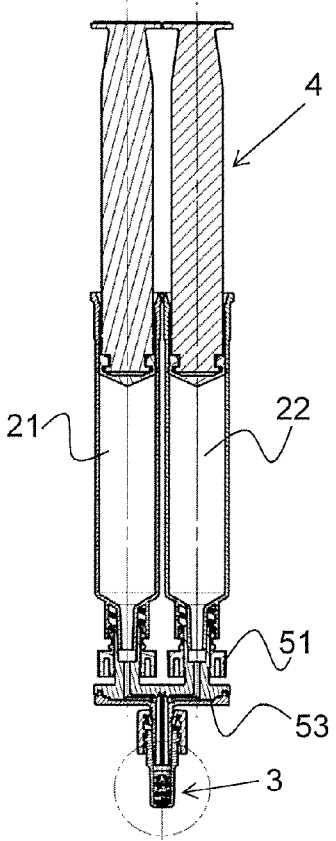
FIG. 5 shows a central sectional view in the plane V-V marked in FIG. 4 of the mixing device of FIG. 1 which is connected to a discharge unit.

The spray head 3, which is in particular a mixing device, consists in the present exemplary embodiment of two components, namely a housing 31 and an insert part 32 which can be inserted into the housing 31. FIG. 2 shows the insert part 32 in a position slightly pulled out of the housing 31 in the proximal direction.

The design of the housing 31 is easy to see in particular in FIGS. 2 and 6 to 10. It comprises, in particular, as far as the design of the closure wall 318 is concerned, a similar design as the mixing and atomizing parts which are disclosed in EP 2 018 132.

The housing 31 comprises as a whole a substantially hollow-cylindrical form which is closed off toward its distal end by means of a closure wall 318. The housing is realized open toward the proximal side, as a result of which inserting the insert part 32 into the interior of the housing 31 is possible.

In the region of its opening which points toward the proximal side, the housing 31 forms a female Luer cone 316. Said female Luer cone 316 serves for connecting the spray head 3 to a discharge unit and in the present exemplary embodiment in particular to the male Luer cone 56 of the connection part 5. To secure the female Luer cone 316 to a male Luer connector, an external thread 319 is provided on the outside surface of the female Luer cone 316. By means of the external thread 319 or the internal thread of the securing sleeve 57 which is realized in a manner that is complementary thereto, the housing 31 can be secured on the connection part 5 when connected to the female Luer cone 54.

A circumferential side wall 317 extends from the female Luer cone 316 in the distal direction. In the present exemplary embodiment, the inside face of the female Luer cone 316, which tapers in the distal direction, is continued progressively inside the side wall 317 by way of its standard 6% taper.

An outlet opening 315 of the spray head 3, through which the two intermixed substances pass from the reservoirs 21, 22 of the syringes 2 toward the outside, are realized inside the closure wall 318. As is described again in detail further below, the two substances are guided to the proximal side of the closure wall 318 in an already mixed form by means of the insert part 32 at one or several points directly in the region of the inside face of the side wall 317. In the present exemplary embodiment, an outlet channel 326 of the insert part 32 opens out on the distal side of the insert part 32 into an annular space 327 which is defined by the insert part 32, the side wall. 317 and the closure wall 318.

Four insert lines 314, which are distributed at regular spacings along the circumferential direction, are realized on the proximal side of the closure wall 318, as is shown in particular in FIGS. 8 and 9. Said insert lines 314 open out into the annular space 327 in each case by way of their region which is arranged radially outside. The insert lines 314 extend from outside to inside initially substantially in the circumferential direction and then via a radially inwardly bent curve open out in a tangential manner into an annular space which is realized concentrically in the closure wall 318 and forms a mixing chamber 311. Four supply channels 313, which are arranged in the circumferential direction spaced apart at regular intervals with respect to one another, extend from the radial inside surface of the mixing chamber 311 offset relative to the insert lines 314 in a tangential manner with respect to a circular vortex chamber 312, which is realized centrally in the closure wall 318. The outlet opening 315 is arranged in the center midpoint of the vortex chamber 312.

The insert lines 314, the mixing chamber 311, the supply channels 313 as well as the vortex chamber 312 are realized in each case all open toward the proximal side of the closure wall 318, and, with the exception of the insert lines 314 which open out into the annular space 327, are completely closed toward the proximal side when the insert part 32 has been inserted in a correct manner into the housing 31 from the distal end face of the insert part 32.

The substances passing from the discharge unit 1 through the insert part 32 into the annular space 327 and from there into the insert lines 314, consequently, when discharging, enter the mixing chamber 311 in the tangential direction where they are additionally mixed together. From the mixing chamber 311 they pass through the supply channels 313 in the tangential direction into the vortex chamber 312 from which they pass in atomized form through the outlet opening 315 to the outside.

The insert part 32 lies, when it is correctly inserted into the housing 31, with its radial outside face abutting sealingly against the inside face of the side wall 317 of the housing 31. As a result of tightening the securing sleeve 57, the housing 31 is pulled in the proximal direction toward the connection part 5, and the insert part 32 is correspondingly pressed into the interior of the housing 31 on account of the stop at the distal end face of the male Luer cone 56. On account of the form of the side wall 317 which tapers slightly in the distal direction in cross section, the insert part 32 is pressed harder against the side wall 317 with its radial outside surface the further it is pressed into the interior of the housing 31. The sealing effect between the housing 31 and the insert part 32 is strengthened as a result.

The insert part 32 comprises as a whole a substantially cylindrical design. It can comprise, but does not have to, a conical design which tapers slightly in the distal direction. In the present embodiment, in particular the proximal end region of the insert part comprises a conical portion which tapers in the distal direction. A circumferential shoulder which serves for forming the annular space 327 is provided in the region of the distal end face of the insert part 32.

In the side circumferential region, that is on the radial outside surface, the insert part 32 comprises a mixing structure 320 with mixing channels 321, 324, 325 and 326 which extends in the distal direction over the entire length of the insert part 32. The mixing structure 320 is designed in a groove-shaped manner, which means that the mixing channels 321, 324, 325 and 326 are realized in each case open toward the outside in the radial direction. Once the insert part 32 has been inserted into the housing 31, the mixing structure 320 however forms mixing channels 321, 324, 325 and 326 in the form of laterally closed, hose-like fluid lines which are defined laterally by the insert part 32 and the inside face of the side wall 317 of the housing 31.

Figure 7:
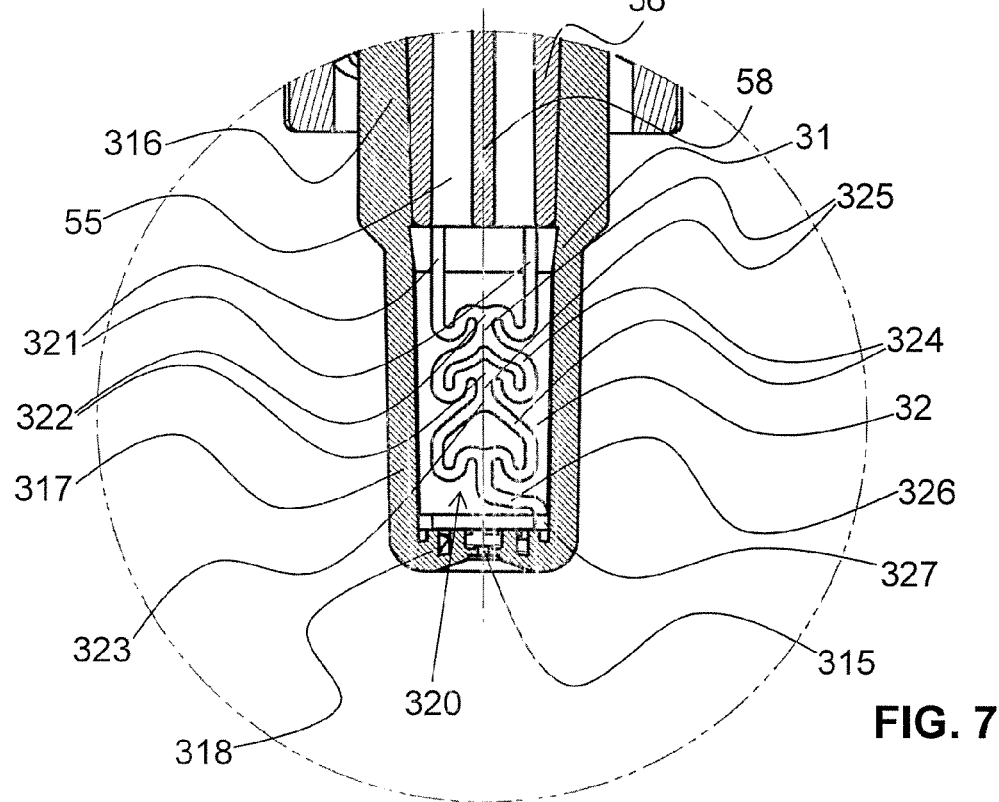
FIG. 7 shows an enlarged part view of the region marked in FIG. 5.
Figure 14:
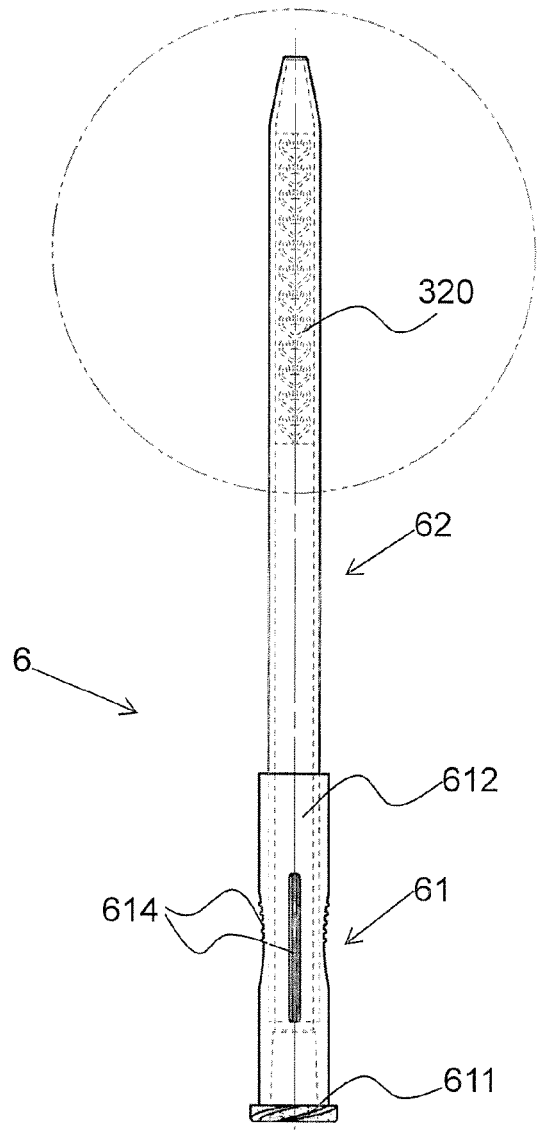
FIG. 14 shows a side view from a line of vision of the mixing device of FIG. 11 which is perpendicular compared to FIG. 11, with the inner workings indicated by way of dotted lines.
Figure 15:
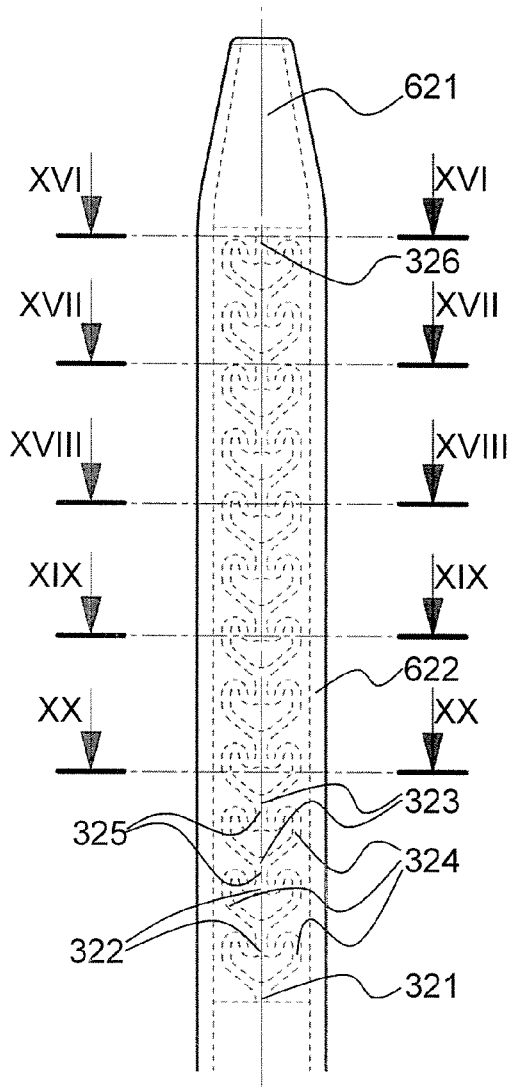
FIG. 15 shows an enlarged part view of the region marked in FIG. 14.
Figure 16:
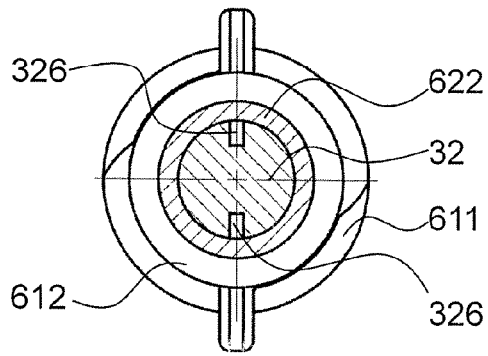
FIG. 16 shows a sectional view in the plane XVI-XVI of the mixing device of FIG. 11 marked in FIG. 15.
Figure 17:
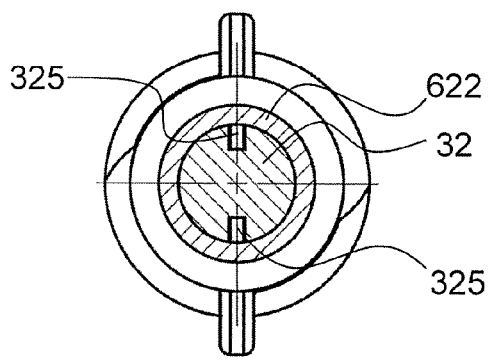
FIG. 17 shows a sectional view in the plane XVII-XVII of the mixing device of FIG. 11 marked in FIG. 15.
Figure 18:
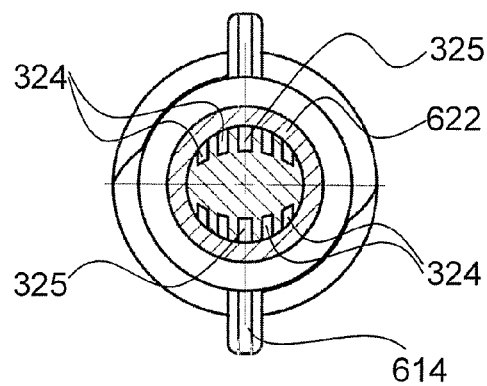
FIG. 18 shows a sectional view in the plane XVIII-XVIII of the mixing device of FIG. 11 marked in FIG. 15.
Figure 19:
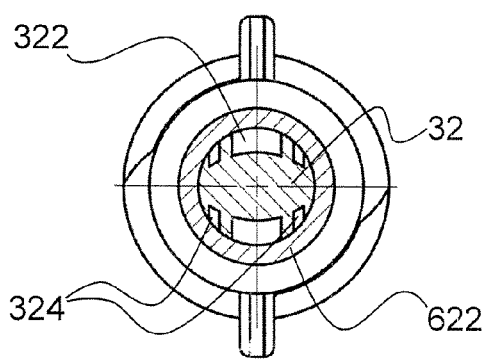
FIG. 19 shows a sectional view in the plane XIX-XIX of the mixing device of FIG. 11 marked in FIG. 15.
Figure 20:
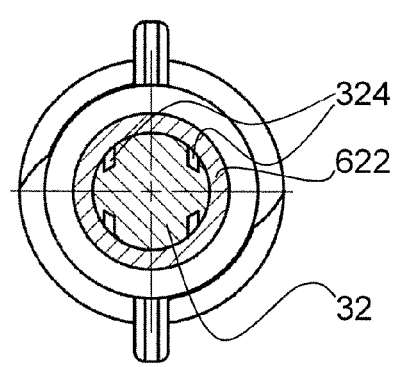
FIG. 20 shows a sectional view in the plane XX-XX of the mixing device of FIG. 11 marked in FIG. 15.
Figure 21:
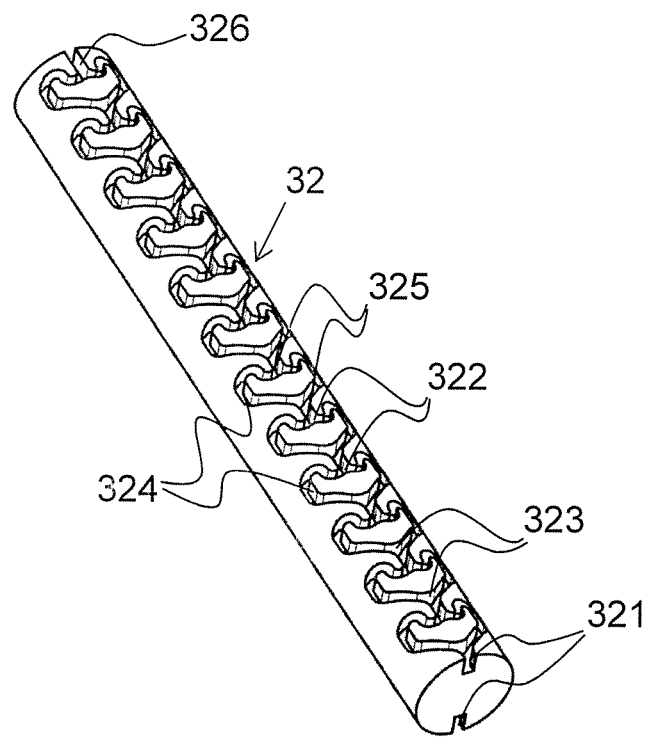
FIG. 21 shows a perspective view of the insert part of the mixing device of FIGS. 11.
Figure 22:
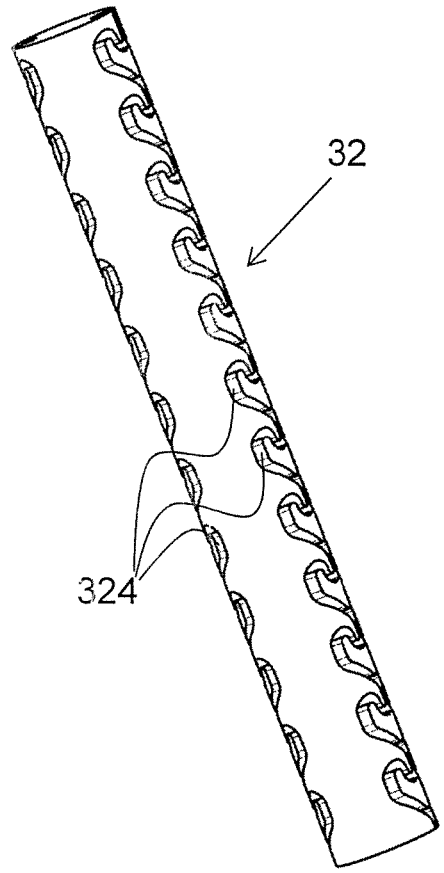
FIG. 22 shows a perspective view from a line of vision of the insert part of the mixing device of FIG. 11 which is modified compared to FIG. 21.

As can be seen in particular from FIG. 7, two feeder channels 321 which extend parallel to one another are realized in the proximal end region of the insert part 32. Said feeder channels 321 open out on the end face of the insert part 32 which points in the proximal direction in, in each case, one of the fluid lines 55 of the connection part 5. In their distal end region, the feeder channels 321 are curved toward one another in each case by almost 180° and in the proximal direction. Via a further bend into the opposite direction, that means specifically a bend of the channels 321 of approximately 90° toward one another and slightly in the distal direction, the two feeder channels 321 open out in each case into a first mixing zone 322. The two substances from in each case one of the reservoirs 21 or 22 come into contact with one another for the first time in said first mixing zone 322. As a result of bringing the two feeder channels 321 together from two directly opposite sides and from directions which are opposite one another, a turbulent flow is generated in the mixing zone 322, as a result of which the two substances are mixed together in an optimum manner.

A first transfer channel 325 extends in the distal direction from the first mixing zone 322. Said first transfer channel 325 opens out at its distal end into a separating region 323 from which two separate channels 324 extend laterally away from one another and slightly in the distal direction. After one portion in which the channels 324 extend in each case parallel to the longitudinal direction of the insert part 32 and consequently to the main flow direction, the channels 342 bend toward one another in each case by approximately 180° such that, at the end of said bend, they extend in the proximal direction substantially parallel to the longitudinal direction of the insert part 32. After said 180° bend, the two channels 324, via in each case a kink, are brought together in such a manner in a second mixing zone 322 that the substances, projected along the longitudinal direction of the insert part 32, pass in each case into the mixing zone 322 in the proximal direction. The two fluid flows meet one another in the second mixing zone 322, once again from two almost directly opposite directions from the channels 324. The mixing zones 322, in this case, can also be designated as turbulent zones.

A further transfer channel 325 extends from the second mixing zone 322 in the distal direction up to a second separating region 323 in which the fluid flow is once again divided into two separate channels 324. Said two channels 324 initially extend away from one another and in the distal direction. They then open out into a third mixing zone 322 via a portion which extends parallel to the longitudinal direction of the insert part 32 and a bend by almost 180° in the proximal direction. It is possible to provide an arbitrary number of further portions of this type, in each case with a separating region, two channels which extend separately from one another and a mixing zone.

An outlet channel 326 extends finally from the third mixing zone 322 in an inclined direction relative to the longitudinal direction of the insert part 32 in the distal direction. In a distal end face of the insert part 32, the outlet channel 326 opens out into the annular space 327. The mouth of the outlet channel 326, in this case, can be located in particular directly opposite one of the mouths of the insert lines 314 of the housing 31.

With the exception of the outlet channel 326, the mixing structure 320 in the present exemplary embodiment is designed as a whole in a mirror-symmetrical manner when viewing the insert part 32 from the side. When the insert part 32 is observed from the side in such a manner that the distal end face of the insert part 32 is arranged at the top and the proximal end face at the bottom, the pairs of channels 324, which extend separately from one another, form in each case the shape of a heart. In the present exemplary embodiment which is easy to see in FIG. 7, two heart-shaped patterns of this type can be seen.

It can be seen from the views in FIGS. 6 and 7 that only one single mixing structure 320, which is arranged on one side on the insert part 32, is provided in the present embodiment. Obviously, it would be possible in an alternative embodiment, for example, to provide two or an even larger number of mixing structures 320 which are situated on the insert part in particular diametrically opposite one another.

FIGS. 11 to 22 show a second embodiment of the present invention. Functionally identically-acting elements are characterized in said embodiment in each case with the same references as in the first embodiment shown in FIGS. 1 to 10.

In the embodiment shown in FIGS. 11 to 22, the mixing device is not realized as a spray head 3 as in FIGS. 1 to 10, but as a cannula 6. The cannula 6 comprises a holder 61 as well as a hollow needle 62 which is held in said holder.

The holder 61 comprises a substantially hollow-cylindrical form with a circumferential side wall 612. The hollow needle 62 projects by way of its proximal end region into the interior of the holder 61 and is there fixedly connected to the side wall 612. An external thread 611, by means of which the cannula 6 is connectable to a discharge unit, such as, in particular, the discharge unit 1, by way of the connection part 5, is realized in the proximal end region of the side wall 612. The external thread 611, in this case, surrounds a female Luer cone 613. Grip structures 614 are additionally realized on the outside surface of the side wall 612 in order to facilitate the handling of the cannula 6.

The hollow needle 62 is realized as a whole in a substantially hollow-cylindrical manner with a circumferential side wall 622. The hollow needle 62 comprises an outlet opening 621 at its distal, tapering end.

As can be seen in particular from FIG. 13, an insert part 32, which abuts in particular in a sealing manner against the inside face of the side wall 612, is inserted into the interior of the hollow needle 62. Two mixing structures, which are designed in a substantially similar manner to the mixing structure 320 of the first embodiment shown in FIG. 7, are realized on the outside surface of the insert part 32, on diametrically opposite sides. Contrary to the mixing structure 320 of the first embodiment, the two mixing structures 320 of the present embodiment, however, comprise only one feeder channel 321. Said feeder channel 321 opens out directly in each case into a first separating region 323. The mixing structures 320 of the present embodiment also comprise in each case, compared to the mixing structure shown in FIG. 7, a much larger number of pairs of channels 324 which extend separately from one another and which form in each case a heart-shaped pattern. In the present case there is a total of 12 such pairs of channels 324.

In the present embodiments, the housing 31, the holder and in particular the insert part 32 are in each case produced integrally from a plastics material using an injection molding method. The mixing structure 320 can be milled into the outside surface of the insert part 32 during production. It can, however, also be produced using the injection molding method by means of a correspondingly realized mold.

Obviously, the invention described here is not limited to the mentioned embodiments and a plurality of modifications are possible. Thus, for example, the mixing structure does not forcibly have to be realized on the outside surface of the insert part. It could also be formed, for example, by mixing channels which extend fully in the interior of the insert part. In an alternative embodiment, the insert part 32 could also be realized integrally together with the housing 31 or the hollow needle 62. For the connection of the spray head 3 or the cannula 6 to the discharge unit, a plurality of other connections known to the skilled person are conceivable in place of a Luer connector. The discharge unit does not absolutely have to be realized as two interconnected individual syringes, but it could, for example, also be a double or multiple syringe or also a single syringe where the two substances are certainly accommodated in the same reservoir, but not yet in a sufficiently mixed state. A plurality of further modifications are conceivable.

REFERENCE NUMERALS

| | |
|---|---|
| 1 | Discharge unit |
| 2 | Syringe |
| 21, 22 | Reservoir |
| 23 | Male Luer cone |
| 24 | Securing sleeve |
| 3 | Spray head |
| 31 | Housing |
| 311 | Mixing chamber |
| 312 | Vortex chamber |
| 313 | Supply channel |
| 314 | Insert line |
| 315 | Outlet opening |
| 316 | Female Luer cone |
| 317 | Side wall |
| 318 | Closure wall |
| 319 | External thread |
| 32 | Insert part |

-continued

| | |
|---|---|
| 320 | Mixing structure |
| 321 | Feeder channel |
| 322 | Mixing Zone |
| 323 | Separating region |
| 324 | Channel |
| 325 | Transfer channel |
| 326 | Outlet channel |
| 327 | Annular space |
| 4 | Piston |
| 5 | Connection part |
| 51 | Rotational element |
| 52 | Threaded sleeve |
| 53 | Housing |
| 54 | Female Luer cone |
| 55 | Fluid line |
| 56 | Male Luer cone |
| 57 | Securing sleeve |
| 58 | Parting wall |
| 6 | Cannula |
| 61 | Holder |
| 611 | External thread |
| 612 | Side wall |
| 613 | Female Luer cone |
| 614 | Grip structure |
| 62 | Hollow needle |
| 621 | Outlet opening |
| 622 | Side wall |

The invention claimed is:

1. A mixing device which is connectable to a discharge unit and which, when one or more substances are discharged from the discharge unit, serves for mixing said substances, said mixing device comprising
a base element with a circumferential side wall as well as
an insert part comprising an outside surface, a circumferential region and a mixing structure with mixing channels, through which the substances can be discharged out of the discharge unit,
wherein the insert part is insertable into the base element in such a manner that it abuts sealingly against the side wall of the base element by way of a large part of its entire circumferential region,
wherein the mixing structure is realized with its mixing channels in the form of indentations in the outside surface of the insert part such that the insert part, when being inserted in the base element, together with the circumferential side wall of the base element delimits the mixing channels,
wherein the mixing structure comprises at least one pair of two channels which extend separately from one another as well as a mixing zone into which the two channels, which extend separately from one another, open out,
wherein the mixing device comprises a main flow direction along which the substances are discharged through the mixing device,
and wherein the two channels, which extend separately from one another, projected onto said main flow direction, extend both in the main flow direction and in the direction pointing opposite to the main flow direction.

2. The mixing device as claimed in claim 1, wherein the mixing structure is realized at the side in the circumferential region of the insert part.

3. The mixing device as claimed in claim 1, wherein the insert part abuts sealingly against the side wall of the base element by way of at least 50%, in particular by way of at least 70%, of its circumferential surface.

4. The mixing device as claimed in claim 1, wherein the two channels, which extend separately from one another, open out into the mixing zone in such a manner that the substances pass into the mixing zone from directions which are substantially opposite one another.

5. The mixing device as claimed in claim 1, wherein the mixing structure comprises at least one transfer channel and one separating region into which the transfer channel opens out and from which the two channels, which extend separately from one another, extend.

6. The mixing device as claimed in claim 5, wherein the mixing structure comprises several pairs of channels, which extend separately from one another, and several mixing zones into which in each case the two channels of one pair, which extend separately from one another, open out, and wherein the transfer channel connects a mixing zone and a separating region together.

7. The mixing device as claimed in claim 6, wherein the mixing structure comprises at least three, in particular at least five, pairs of channels, which extend separately from one another, and at least three, in particular at least five, mixing zones into which in each case the two channels of one pair, which extend separately from one another, open out.

8. The mixing device as claimed in claim 1, wherein the insert part as a whole has a substantially cylindrical form.

9. The mixing device as claimed in claim 1, wherein a mixing chamber and a vortex chamber are realized in the base element.

10. The mixing device as claimed in claim 1, wherein several substantially identical mixing structures are realized on the insert part.

11. The mixing device as claimed in claim 1, wherein the mixing device comprises a Luer connection which serves for connecting the mixing device to the discharge unit.

12. A set comprising a discharge unit and a mixing device, wherein the mixing device is connectable to the discharge unit in such a manner that one or several substances can be discharged out of the discharge unit through the mixing device and at the same time can be mixed in the mixing device, the mixing device comprising
a base element with a circumferential side wall as well as
an insert part comprising an outside surface, a circumferential region and a mixing structure with mixing channels, through which the substances can be discharged out of the discharge unit,
wherein the insert part is insertable into the base element in such a manner that it abuts sealingly against the side wall of the base element by way of a large part of its entire circumferential region,
wherein the mixing structure is realized with its mixing channels in the form of indentations in the outside surface of the insert part such that the insert part, when being inserted in the base element, together with the circumferential side wall of the base element delimits the mixing channels,
wherein the mixing structure comprises at least one pair of two channels which extend separately from one another as well as a mixing zone into which the two channels, which extend separately from one another, open out,
wherein the mixing device comprises a main flow direction along which the substances are discharged through the mixing device,
and wherein the two channels, which extend separately from one another, projected onto said main flow direction, extend both in the main flow direction and in the direction pointing opposite to the main flow direction.

13. The set as claimed in claim 12, wherein the discharge unit is a double syringe, a multiple syringe or several individual syringes connected together.

* * * * *